United States Patent [19]

Bugaj et al.

[11] Patent Number: 4,707,353

[45] Date of Patent: Nov. 17, 1987

[54] RADIOGRAPHIC IMAGING AGENTS

[75] Inventors: Joseph E. Bugaj, Harrison; Terry W. Grogg, Cincinnati, both of Ohio

[73] Assignee: Mallinckrodt, Inc., St. Louis, Mo.

[21] Appl. No.: 735,288

[22] Filed: May 17, 1985

Related U.S. Application Data

[63] Continuation of Ser. No. 447,862, Dec. 8, 1982, abandoned.

[51] Int. Cl.⁴ .................... A61K 43/00; A61K 49/02; A61K 49/00
[52] U.S. Cl. ......................................... 424/1.1; 424/9; 534/14; 514/493
[58] Field of Search .................... 424/1.1, 9; 514/493, 514/108; 534/14; 252/188.31

[56] References Cited

U.S. PATENT DOCUMENTS

| | | | |
|---|---|---|---|
| 3,749,556 | 7/1973 | Barak et al. | 424/1.1 |
| 3,902,849 | 9/1975 | Barak et al. | 424/1.1 |
| 4,229,427 | 10/1980 | Whitehouse | 424/1.1 |
| 4,232,000 | 11/1980 | Fawzi | 424/1.1 |
| 4,233,284 | 11/1980 | Fawzi | 424/1.1 |
| 4,243,652 | 1/1981 | Francis | 424/1.1 |
| 4,247,534 | 1/1981 | Bevan | 424/1.1 |
| 4,311,689 | 1/1982 | Ruddock | 424/1.1 |
| 4,314,986 | 2/1982 | Ruddock | 424/1.1 |
| 4,364,920 | 12/1982 | Winchell | 424/1.1 |
| 4,427,647 | 1/1984 | Brockas et al. | 424/1.1 |
| 4,439,413 | 3/1984 | Hayashi et al. | 424/1.1 |
| 4,440,738 | 4/1984 | Fawzi et al. | 424/1.1 |
| 4,451,451 | 5/1984 | Rimmer | 424/1.1 |
| 4,489,053 | 12/1984 | Azuma et al. | 424/1.1 |
| 4,497,744 | 2/1985 | Fawzi | 424/1.1 |
| 4,504,462 | 3/1985 | Van Duzee et al. | 424/1.1 |
| 4,504,463 | 3/1985 | Van Duzee | 424/1.1 |
| 4,510,125 | 4/1985 | Grogg et al. | 424/1.1 |

FOREIGN PATENT DOCUMENTS

| | | | |
|---|---|---|---|
| 46,067 | 2/1982 | European Pat. Off. | 424/1.1 |
| 2,618,337 | 11/1976 | Fed. Rep. of Germany | 421/1.1 |
| 1489330 | 10/1977 | United Kingdom | 424/1.1 |
| 1541070 | 2/1979 | United Kingdom | 424/1.1 |

OTHER PUBLICATIONS

Kempi, et al., "99mtc-DTPA(Sn) Dry Kit Preparation", Nuclear Medizin, 13, 389-399 (1975).

Tomita, et al., "The Preparation of 99mTc-sulfur-colloid by Reduction with Metallic Tin", Radioisotopes, 25, 49-50 (1975).

Persson, et al., "Labelling Plasmin with Technetium-99m for Scintigraphic Localization of Thrombi", Intl. J. of Applied Radiation & Isotopes, 28, 97-104 (1977).

Ikeda, et al., "A New Preparation Method for 99mTc–Phytate", J. of Nuclear Medicine, 17, 389-393 (1976).

van den Brand, et al., "The Influence of Experimental Conditions of the Formation of Various 99mTc(Sn)EHDP Complexes", Intl. J. of Applied Radiation & Isotopes, 33, 39-45 (1982).

Tofe et al., *Journal of Nuclear Medicine*, vol. 21, No. 4, pp. 366-370, Apr. 1980.

Tofe et al., *Journal of Nuclear Medicine*, vol. 17, No. 9, pp. 820-825, Sep. 1976.

Winchell et al., *Chemical Abstracts*, vol. 91, No. 19, p. 278, Nov. 5, 1979.

Tofe, et al., *Radiopharmaceuticals* 2: Proceedings, 2nd International Symposium, pp. 637-644, Seattle, Washington, Mar. 19-22, 1979.

*Primary Examiner*—John F. Terapane
*Assistant Examiner*—J. E. Thomas
*Attorney, Agent, or Firm*—Bernard, Rothwell & Brown

[57] ABSTRACT

A composition useful for tissue imaging, comprising tin metal or an alloy containing tin and an ascorbate, gentisate or reductate stabilizer. Preferably, such compositions also comprise a tissue-specific carrier and a stannous compound.

14 Claims, No Drawings

RADIOGRAPHIC IMAGING AGENTS

This is a continuation of application Ser. No. 447,862 filed Dec. 8, 1982, now abandoned.

BACKGROUND OF THE INVENTION

This invention relates to compositions useful in the preparation of radiodiagnostic agents for use in imaging and assay procedures. More particularly, it relates to compositions and processes used in preparing improved technetium-based tissue imaging agents.

Scintigraphic skeletal imaging and similar radiographic techniques for visualizing other tissues are finding ever-increasing application in biological and medical research and in diagnostic procedures. Generally, scintigraphic procedures involve the preparation of radioactive agents which, upon introduction into a biological subject, become localized in specific organs, tissues, or skeletal structures that are under study. When so localized, traces, plots, or scintiphotos of the distribution of the radiographic materials can be made by various radiation detectors, e.g., traversing scanners and scintilation cameras. The distribution and corresponding relative intensity of the detected radioactive material not only indicates the position occupied by the tissue in which the radionuclide is localized, but also indicates the presence of aberrations, pathological conditions, and the like.

In general, depending on the type of radionuclide used and the organ of interest, a scintigraphic imaging agent as used in a hospital comprises a radionuclide, a carrier agent designed to target the specific organ, various auxiliary agents which affix the radionuclide to the carrier, water or other delivery vehicles suitable for injection into, or aspiration by, the patient, physiologic buffers and salts, and the like. In most cases, the carrier attaches or complexes with the radionuclide and localizes the material in a location other than where the radionuclide itself would naturally concentrate in a biologic subject. However, certain radionuclides may be used without an additional carrier, such as thallium-201 ($^{201}$Tl), for myocardial localization, and technetium-99m ($^{99m}$Tc), in pertechnetate form, for brain and thyroid imaging.

The tissue imaging agents of the instant invention incorporate technetium-99m as the radionuclide, complexed or coordinated with a tissue-specific carrier. This man-made radionuclide, which is formed in the radioactive decay of molybdenum-99, is commercially produced in "generators" by eluting a saline solution through a matrix containing molybdenum-99. The metastable technetium isotope in such eluates is found in the chemically-stable, oxidized, pertechnetate form ($^{99m}$TcO$_4^-$, hereinafter "pertechnetate-Tc99m"). However, the technetium in pertechnetate has a valence state of +7 and will not complex with the most commonly used carriers for radionuclide tissue imaging. This problem is easily overcome by reducing the technetium to a lower (+5, +4 and, most commonly, +3) oxidation state. Thus, technetium-labelled imaging agents are generally prepared by admixing pertechnetate-Tc99m isotonic saline solution with a technetium reductant (reducing agent). The ferrous and chromous salts, and the stannous salts (as are used in most commercial applications), of sulfuric and hydrochloric acid are known reductants for use in tissue imaging agents. For example, U.S. Pat. No. 3,983,227. Tofe and Francis, issued Sept. 28, 1976 discloses the use of such reducing salts, along with organophosphonate bone-seeking carriers, to prepare technetium-based skeletal imaging agents. U.S. Pat. No. 4,311,689, Ruddock, issued Jan. 19, 1982, describes the use of metallic tin as a reducing agent for pertechnetate, in tissue imaging compositions. Similarly, U.S. Pat. No. 4,314,986, Ruddock, issued Feb. 9, 1982, describes the use of metallic tin, and a soluble salt of a metal below tin on the electrochemical series, in tissue imaging compositions.

Such technetium-containing scintigraphic imaging agents are known to be unstable in the presence of oxygen, primarily since oxidation of the reductant and/or the technetium destroys the reduced technetium/targeting carrier complex. Accordingly, imaging agents are generally made oxygen-free by saturating the compositions with oxygen-free nitrogen gas or by preparing the agents in an oxygen-free atmosphere. Stabilization of imaging agents can also be achieved through chemical means. U.S. Pat. No. 4,232,000. Fawzi, issued Nov. 4, 1980, discloses the use of gentisyl alcohol as a stabilizer for technetium imaging agents. Similarly, U.S. Pat. No. 4,233,284, Fawzi, issued Nov. 11, 1980, discloses the use of gentisic acid as a stabilizer. German Offenlegungsschrift No. 2,618,337. Tofe, published Nov. 11, 1976, discloses the use of ascorbic acid and erythorbic acid as stabilizers with technetium imaging agents. U.S. patent application Ser. No. 387,138, Fawzi, et al., filed June 10, 1982, discloses the use of reductate stabilizers such as reductic acid, methyl reductic acid, and 6-bromo-6-deoxyascorbic acid, in imaging agents. European Patent Application Publication No. 46,067, Brockas, et al., published Feb. 17, 1982, describes compositions for use in tissue imaging that contain metallic tin or stannous salts as pertechnetate reducing agents together with nitrate or nitrite stabilizers.

It has now been discovered that the combination of metallic tin and certain stabilizing compounds is an effective reducing system for use in technetium-based tissue imaging compositions. Thus, the combination of tin metal and stabilizer reduces the technetium in commercially produced technetium-Tc99m solutions and maintains the technetium in a reduced state so as to allow formation of stable and useful complexes with tissue-specific carriers. (While the stabilizing compounds can, themselves, serve as tissue-specific carriers, additional carrier compounds are preferably included in the compositions of this invention.) The tissue imaging agents thereby formed have use characteristics superior to those of agents containing stannous salts alone, stannous salts and stabilizers, metallic tin alone, or metallic tin and nitrate or nitrite salts, with respect to chemical stability of the technetium/carrier complex and/or biologic performance.

The combination of tin metal and stabilizer can also be used in in vitro assay procedures such as radioimmunoassay (RIA). RIA allows the measurement of picogram ($10^{-12}$ gram) quantities of antigens through labelling such antigens with a radioisotope. RIA procedures are described in Hunter, "Radioimmunoassay," *Handbook of Experimental Immunology*, Vol. 1, 2nd ed., (Wein, editor), 17.1–17.36 (1973). As an alternative to RIA procedures that use radioisotopes such as I$^{131}$ and I$^{125}$, antigens can be labelled with technetium-99m, prepared from commercially-available pertechnetate-Tc99m solutions through reduction by the tin metal/stabilizer compositions of the present invention.

SUMMARY OF THE INVENTION

The present invention provides highly stable compositions useful in the preparation of imaging and assay agents containing technetium-99m. The compositions of the present invention comprise free, elemental tin ($Sn^0$), in such form as metallic tin or an alloy containing tin (hereinafter "tin metal"), and an effective amount of a stabilizing compound selected from the group consisting of gentisic acid, gentisyl alcohol, hydroquinone, ascorbic acid, erythorbic acid, and reductic acid and certain compounds structurally-related to reductic acid, and pharmaceutically-acceptable salts, esters, amides, and mixtures thereof (hereinafter "stabilizers"). Such compositions preferably further comprise an optional stannous compound that contributes stannous ions in aqueous solution.

The compositions of this invention are useful in the process of making stable technetium-based radiographic tissue imaging agents and in radioimmunoassay procedures. Imaging agents can be formed by adding a pertechnetate-Tc99m to the combination of tin metal and stabilizer, whereby the stabilizing compound also serves as a tissue-specific carrier. Preferably, an additional (optional) carrier compound is incorporated into such compositions, either at the time of manufacture or at the time of use, to form a tissue-specific agent containing a stable complex of technetium-99m with the optional carrier compound.

Such compositions that contain diphosphonate bone-seeking carriers yield stable skeletal imaging agents with superior imaging properties as compared to systems described in the art. This improved performance is manifested through faster blood clearance and higher relative skeletal uptake of the technetium radioisotope, i.e., the bone targeting carrier, complexed with technetium-99m, is more quickly removed from the blood and is less concentrated in soft tissues than carrier agents described in the art.

DESCRIPTION OF THE INVENTION

Systems and methods which are useful to produce technetium/carrier complexes from commercially available pertechnetate-Tc99m generator solutions must exhibit the following properties:
1. Toxicological acceptability under conditions of use;
2. The ability to reduce technetium and maintain the product in stable form for a reasonable period of storage and/or under use conditions; and
3. No substantial interference with the delivery of the technetium radionuclide to the intended body tissues.

As described herein, the combination of tin metal with certain stabilizers meets all of the above three criteria. Components, processes and methods useful in forming the imaging agents and other compositional forms of this invention are described below.

As used herein, the term "imaging" refers to all radiographic tissue imaging processes and assay procedures for which the instant compositions may be used, including (but not limited to) skeletal imaging. Such processes may be in vivo or in vitro. The term "imaging agent" refers to compositions useful for imaging, including (but not limited to) skeltal imaging, such compositions comprising the product of admixing pertechnetate-Tc99m, or other useful radioisotope, to an imaging kit at least comprising tin metal and a stabilizer.

There are several compositional aspects to the present invention. In one aspect, compositions of the present invention comprise tin metal and a stabilizer. In a second aspect, compositions of this invention comprise a pertechnetate-Tc99m solution having dissolved therein an effective amount of a stabilizer while the solution is in contact with tin metal. Other compositions of this invention further comprise a tissue-targeting carrier which attaches/complexes with technetium-99m and localizes the radionuclide in a particular body organ or tissue. One preferred aspect of such a composition comprises a tissue-targeting carrier, tin metal and a stabilizer in an "imaging kit" or "kit," as referred to herein. An imaging agent, then, is formed by addition of a pertechnetate-Tc99m solution.

Kits, and other compositions of this invention for use commercially, preferably contain sufficient material to form multiple doses of imaging agent. Obviously, the amount of material to be incorporated in such compositions will depend upon the number and size of doses of imaging agent desired. Further, specific quantities of metal, stabilizer, optional carrier, and optional stannous compound may vary according to the particular compounds used, and the quantity of pertechnetate-Tc99m to be added to the composition. (As used herein, the term "single-dose agent" refers to an agent reconstituted from a kit comprising such amounts of tin metal, stabilizer, and optional ingredients, with pertechnetate-Tc99m, so as to be suitable for injection of the agent, in entirety, into a human adult.) The practitioner of this invention may determine appropriate quantities by reference to literature describing particular carriers and stabilizer compounds described herein.

COMPONENTS

Metals:

The compositions and processes of this invention incorporate tin metal which, in combination with a stabilizer, effects a substantially complete reduction of technetium in a pertechnetate solution. Commercial or analytical grade tin may be used, i.e., the metallic tin may be substantially 100% pure or may incorporate trace quantities of other metals. Various alloys of tin with other metals are also useful in this invention, including alloys containing as little as 5% tin, if not less. In particular, alloys of tin with gold and silver are suitable.

In general, small quantities of pertechnetate-Tc99m will be used with these compositions. Thus, the quantity of tin metal present in the instant composition required to effect complete reduction of all of the technetium to be added in forming an imaging agent is also quite small. However, the quantity of metal actually to be used in the instant compositions will vary according to the various physical characteristics of the piece of metal itself and will have an effect not only on the ability to ensure complete reduction of the radioisotope, but also in the speed in which the reduction is effected. Such physical characteristics include:
(1) the quantity (weight) of metal added;
(2) the composition of metal, i.e., the percent of metal that is tin metal;
(3) the shape and form of the metal added, i.e., the available surface area exposed to the stabilizer in a pertechnetate solution; and
(4) the surface condition of the metal.

It should be noted that parameters 3 and 4 listed above are interrelated in the sense that the presence of impurities and irregularities on the surface of the metal will have an effect on the available total surface area exposed to the pertechnetate-Tc99m solution. Pre-treatment of the metal surface through exposure to an acid (e.g., hydrochloric, sulfuric, or nitric acid) followed by washing with ethanol, for example, may remove such impurities and affect the performance of the metal/-stabilizer combination.

For most purposes, the total surface area of tin metal effective to reduce the technetium in the pertechnetate-Tc99m of a single-dose agent is from about 2 mm$^2$ to about 1000 mm$^2$. While tin metal amounts toward the upper end of this range are in excess of that needed to completely reduce the technetium, and variance thereof is not likely to effect the completeness or rate of reduction, variance of the minimum amount of tin metal may have an effect on the completeness of technetium reduction and the speed of the reduction reaction. Preferred amounts of tin metal in a single-dose agent have a total surface area of from about 20 mm$^2$ to about 180 mm$^2$, most preferably from about 80 mm$^2$ to about 120 mm$^2$.

The tin metal may be present in a foil, granule, wire, shot or any other convenient form. When the metal is not physically fixed to the container into which the pertechnetate-Tc99m solution is to be added, care must be taken so as to filter the loose metal from the imaging agent when it is withdrawn for injection into a subject. Thus, these problems can be obviated by affixing the metal to a vessel. For example, the vessel in which the imaging agent is formed may be coated with the tin metal or the vessel itself may be composed entirely or in part of the metal. For example, the interior surfaces of a glass vial can be coated with tin by such methods as electrodepositing, spraying, condensing, sputtering, and plating. Various forms and arrangements of metallic tin in such vessels are described in U.S. Pat. No. 4,311,689, Ruddock, issued Jan. 19, 1982 (incorporated by reference herein).

Stabilizers:

The compositions and processes of this invention incorporate an amount, herein "stabilizing amount," of a stabilizer material sufficient to yield (in combination with tin metal) substantially complete reduction of all technetium radioisotope to be added to the ultimately-formed imaging agent compositions, and to maintain the technetium in a reduced state. These stabilizers may have the added benefit of reducing the formation of technetium-labelled impurities which may form during the production and use of such imaging agents.

Compounds (herein "gentisate compounds") that can be used as stabilizers in the instant invention include: hydroquinone, gentisyl alcohol, gentisic acid, and the pharmaceutically-acceptable salts and esters thereof. "Ascorbate compounds" that are also useful include: ascorbic acid, erythorbic acid, substituted 5-deoxyascorbic acid, substituted 5-deoxyerythorbic acid, substituted 6-deoxyascorbic acid, substituted 6-deoxyerythorbic acid, nicotinic acid and nicotinamide complexes thereof, and the pharmaceutically-acceptable salts and esters thereof. These compounds are described in the following documents, all incorporated by reference herein: U.S. Pat. Nos. 4,229,427, Whitehouse, issued Oct. 21, 1980 (hydroquinone); 4,232,200, Fawzi, issued Nov. 4, 1980 (gentisyl alcohol); 4,233,284, Fawzi, issued Nov. 11, 1980 (gentisic acid); and German Offenlegungsschrift No. 2,618,337, Tofe, published Nov. 11, 1976 (ascorbic acid).

Ascorbic acid, gentisic acid, sodium ascorbate and sodium gentisate are preferred stabilizers. Gentisic acid is particularly preferred.

Also useful as stabilizers in the instant compositions are "reductate compounds" described in U.S. patent application Ser. No. 387,138, now U.S. Pat. No. 4,440,738, "Stable Radiographic Imaging Agents," Fawzi, et al., filed June 10, 1982 (incorporated by reference herein). Preferred reductate stabilizers for use herein include 6-bromo-6-deoxyascorbic acid, 6-chloro-6-deoxyascorbic acid, sodium-6-bromo-6-deoxyascorbate, sodium-6-chloro-6-deoxyascorbate, reductic acid, sodium reductate, 5-methylreductic acid, sodium-5-methylreductate, and the nicotinic acid and nicotinamide complexes thereof.

As is known in the literature, such stabilizing compounds as ascorbic acid can chelate/complex with technetium and cause it to be deposited in soft tissues of the body. Thus, it will be appreciated that the amount of stabilizer included in the instant compositions should not be so great as to overshadow the tissue-directing effects of the particular tissue-specific optional carriers that might be used in such compositions. Appropriate, substantially non-interfering amounts of stabilizing compounds for use in combination with carriers will vary according to the carrier and/or stabilizer used.

The concentration of the stabilizers utilized in embodiments of this invention will vary depending on the ultimate use of the composition and the concentration of inert or filler materials utilized. (All concentrations herein are defined as percentages, by weight, of stabilizer in pertechnetate solution.) In embodiments of the present invention in which the tin stabilizer is dissolved in a pertechnetate solution, the concentration of stabilizer will vary depending upon the degree of saline dilution. It has been found that stabilizer concentrations greater than about 0.1% interfere with the formation of an acceptable imaging agent. Accordingly, for most purposes where the stabilizer is dissolved in the pertechnetate solution, a concentration no greater than 0.1%, preferably no greater than 0.05%, by weight, is suitable. A concentration within the range of from about 0.01% to about 0.001% is acceptable for many applications. For most purposes where the stabilizer is not dissolved directly in the pertechnetate solution on a technetium generator, from about $2.2 \times 10^{-4}$ mole to about $1.1 \times 10^{-2}$ mole of stabilizer compound is suitable for use in a single-dose agent. Preferably, a single-dose agent contains from about $5.5 \times 10^{-4}$ mole to about $5.5 \times 10^{-3}$ mole of stabilizer compound.

Optional stannous compound:

Compositions of the instant invention optionally contain a water-soluble, pharmaceutically-acceptable compound (herein "stannous compound") that yields stannous ions in an aqueous solution. As a reducing metal cation, stannous ion ($Sn^{+2}$) is known as a reductant for reducing technetium in imaging compositions.

When incorporated into the compositions of the instant invention, stannous compounds facilitate more rapid reduction of the technetium in the pertechnetate-Tc99m used to form imaging agents. Further, stannous compounds increase the stability of the technetium/carrier complex in imaging agents once the agent is withdrawn from the presence of the tin metal prior to injection into a biologic subject. However, the quantity of stannous compound optionally incorporated into the instant compositions is kept low so as to avoid deleterious effects on the biological performance of imaging agents formed. See U.S. patent application Ser. No. 387,135, now abandoned, "Radiographic Imaging Agents," Benedict and VanDuzee, filed June 10, 1982

(incorporated by reference herein), and U.S. patent application Ser. No. 387,137, now abandoned "Radiographic Imaging Agents," VanDuzee, filed June 10, 1982 (incorporated by reference herein). U.S. patent application Ser. No. 387,137, now abandoned, describes a composition comprising a stannous compound and a diphosphonate tissue-specific carrier wherein the molar ratio of the diphosphonate carrier to stannous compound is at least 65:1.

Stannous compounds useful herein include stannous chloride, stannous fluoride, stannous citrate, and stannous tartrate. Of these, stannous chloride is particularly preferred. The use of stannous salts in imaging compositions is described in U.S. Pat. No. 3,983,227, Tofe and Francis, issued Sept. 28, 1976 (incorporated by reference herein).

A preferred stannous compound is stannous oxide. It is particularly preferred to incorporate stannous oxide as a coating on the tin metal. As an oxidation product of tin, stannous oxide is usually present on the surface of tin metal and, in practice, may be naturally present in the compositions of this invention, since complete removal of the oxide from the surface of tin metal is commercially difficult. Stannous oxide can also be incorporated in the compositions and processes of the instant invention through deliberate oxidation of tin metal. It should be noted that if stannous oxide is incorporated as an optional stannous compound, in the form of a naturally-occurring coating on the tin metal, acid pre-treatment may be undesirable since the oxide coating could be substantially removed.

Optional Carriers:

Compositions of the present invention may also contain compounds which complex with technetium radionuclide and localize the radionuclide in particular body tissues and organs. Broadly speaking, there are two classes of such carrier agents: those which target soft tissue organs such as the heart, marrow, liver, spleen, kidneys and lungs; and those which target calcified tissue, such as bone and other tissues which may be undergoing pathological calcification. Examples of such carriers or targeting agents include:

1. Diethylenetriamine pentaacetate (DTPA), gluconate, and glucoheptonate for brain imaging;
2. DTPA, gluconate, glucoheptonate, dimercaptosuccinate (DMSA), ascorbate and citrate for kidney imaging;
3. Diphosphonates and pyrophosphates for myocardial infarct imaging;
4. N-2,6(dimethyl phenyl)carbamoylmethyliminodiacetic acid (HIDA) and diethyl HIDA for hepatobiliary imaging;
5. Fibrinogen, streptokinase, and urokinase for deep vein thrombus detection (DVT);
6. Human serum albumin for blood pool visualization;
7. Macroaggregated albumin and albumin microspheres for lung imaging;
8. Stabilized colloids, PVP, and dextran for liver imaging; and
9. Water-soluble phosphates and phosphonates for skeletal imaging.

It should be noted that certain stabilizers may also complex with technetium and, thus, serve also as carriers in the instant compositions. For example, ascorbic acid can be incorporated into the instant invention both as a stabilizer and as a carrier, yielding a renal imaging agent.

Preferred embodiments of the instant invention are used in skeletal imaging. The operable mono-, di-, and polyphosphonates particularly useful as bone-specific carriers are described in U.S. Pat. No. 3,983,227, Tofe, et al., issued Sept. 28, 1976 (incorporated by reference herein) and U.S. Pat. No. 4,247,534, Bevan, issued Jan. 27, 1981 (incorporated by reference herein).

Preferred bone-specific diphosphonate carriers for use herein include compounds and mixtures of compounds selected from the group consisting of:

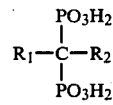

wherein $R_1$ is hydrogen, alkyl containing from 1 to about 20 carbon atoms, aminoalkyl, substituted aminoalkyl, alkenyl containing from 2 to about 20 carbon atoms, aryl (e.g., phenyl, naphthyl), phenylethenyl, benzyl, halogen (e.g., chlorine, bromine and fluorine), hydroxyl, amino, substituted amino (e.g., methylamino, dimethylamino, diethylamino, N-hydroxy-N-ethylamino, acetylamino), $-CH_2COOH$, $-CH(COOH)CH_2COOH$, $-CH_2PO_3H_2$, $-CH(PO_3H_2)(OH)$, or $-(CH_2C(PO_3H_2)_2)_n-H$ where $n=1$ to 15, $R_2$ is hydrogen, lower alkyl (e.g., methyl, ethyl, propyl and butyl), amino, benzyl, halogen (e.g., chlorine, bromine, and fluorine), hydroxyl, $-CH_2COOH$, $-CH_2PO_3H_2$, or $-CH_2CH_2PO_3H_2$, and the pharmaceutically-acceptable salts thereof. The stannous salts thereof are also useful as stannous compounds, as described above. Particularly preferred diphosphonates include methane diphosphonic acid (MDP), methane hydroxydiphosphonic acid (HMDP), and ethane-1-hydroxy-1,1-diphosphonic acid (EHDP). HMDP is a most preferred carrier.

Also particularly preferred are the aminodiphosphonate compounds further described in U.S. patent application Ser. No. 387,135, Benedict and Van Duzee, "Radiographic Imaging Agents," filed June 10, 1982 (incorporated by reference herein). Most preferred aminodiphosphonate carriers include methaneamino diphosphonic acid (AMDP), methane-N-methyl amino diphosphonic acid, methane-N,N-dimethylamino diphosphonic acid, propane-1-hydroxy-3-amino-1,1-diphosphonic acid, and ethane-1-hydroxy-2-amino-1,1-diphosphonic acid.

U.S. Pat. No. 4,016,249, Adler, et al., issued Apr. 5, 1977, incorporated by reference herein, contains a succinct disclosure of the use of inorganic phosphates of various types in the manufacture of skeletal imaging agents. In particular, certain soluble pyrophosphate species having a molecular weight of less than about 300, said pyrophosphate containing no more than about 25% branched-chain polyphosphate, are quite useful for skeletal imaging. When injected into the patient the pyrophosphate targets bone mineral with the technetium radionuclide, in the manner of the organophosphonates.

Another general class of carriers is made up of proteins, peptides, amino acids, and similar compounds. The size and structures of these compounds make them useful as highly specific carriers for imaging particular tissues. For example, fibrinogen, streptokinase and urokinase are useful for Deep Vein Thrombus (DVT) imaging. Human serum albumin and other blood serum proteins may be used for blood pool imaging, and macroaggregated albumin and albumin microspheres are known for application in lung imaging agents. Whole red blood cells may also be labelled and used for blood pool imaging, and labelled white blood cells used to localize infections. Similarly, technetium imaging of soft tumors may be accomplished through labelling of tumor-specific antibodies. The following documents and articles (all incorporated by reference herein) describe some of the carriers and technetium-based imaging systems in which the compositions and processes of the instant invention are useful: Canadian Pat. No. 1,112,163, Saklad, issued Nov. 10, 1981 (RES imaging using denatured albumin); U.S. Pat. No. 4,305,922, Rhodes, issued Dec. 15, 1981 (ligand exchange method for labelling proteins); U.S. Pat. No. 4,323,546, Crockford, et al., issued Apr. 6, 1982 (radiolabelled compositions for detecting malignant tumors); Sundberg, et al., *Journal of Medicinal Chemistry*, 17, 1364-1367 (1974) (EDTA derivatized proteins for imaging tumors); and Eckelman, et al., *Cancer Research*, 40, 3036-3042 (1980) (radiopharmaceuticals labelled with technetium).

COMPOSITIONS, PROCESSES, AND METHODS

The imaging agents made with the compositions of this invention are intended for intraveneous injection into humans or lower animals. Accordingly, appropriate manufacturing and operating conditions are employed so as to provide suitably sterile, pyrogen-free compositions. Although not necessary to the practice of the present invention, it is preferable to use a pharmaceutically-acceptable extender or filler to dilute the stabilizer and the (optional) carrier and stannous compounds in order to simplify metering the requisite small quantities of such compounds. Sodium chloride and glucose are preferred; sodium chloride is especially preferred inasmuch as its addition will assure that the resulting agent is at least isotonic even if the pertechnetate-Tc99m solution is hypotonic (as is the case when it must be diluted with sterile water to reduce its activity.)

When practicing the instant invention, it is not critical which of the compositional forms of this invention is used to prepare the final technetium-based imaging agent. For example, the stabilizer may be added to the instant compositions in dry-powder form or in solution. Where it is desirable to incorporate the stabilizer directly into the pertechnetate solution, the stabilizer can be simply dissolved either during or after elution of pertechnetate from the generator. The elution process is thoroughly described in U.S. Pat. No. 3,369,121, issued Feb. 13, 1968, (incorporated by reference herein). The metal can then be added directly to the stabilizer-containing generator eluate.

The present invention also encompasses an improved method of preparing technetium-based imaging agents comprising dissolving a stabilizer in a pertechnetate solution in the presence of metal. Optional carriers and stannous compounds can be co-dissolved with the stabilizer, either simultaneously or sequentially. Either co-dissolving procedure results in an improved technetium-based imaging agent. In one mode of this process, the metal may be incorporated in the column of the pertechnetate generator. The stabilizer, and optional components, can be dissolved in the pertechnetate eluate by dissolving the compounds in the saline used to elute the pertechnetate. Similar processes are described in U.S. Pat. No. 3,749,556, Barak, et al., issued July 31, 1973 (incorporated by reference herein) and U.S. Pat. No. 3,902,849, Barak, et al., issued Sept. 2, 1975 (incorporated by reference herein). Alternatively the stabilizer and optional components may be incorporated into the generator column along with the metal. These components might be coated onto an inert substrate or the generator vessel itself above, below, or coextensive with tin metal in the generator column. Combinations of the above process modes may also be used.

In a preferred embodiment of the present invention, a stable technetium-bases skeletal imaging agent can be formed by the direct addition of a pertechnetate solution to a composition "kit" comprising: a stabilizer; tin metal; and a skeletal-specific carrier compound selected from the mono-, di-, or polyphosphonates, as described above.

A particularly preferred composition of this invention comprises:

(1) a diphosphonate carrier;
(2) a stabilizer;
(3) a tin metal; and
(4) a stannous compound.

The quantity of these components incorporated into a preferred kit is enough to form multiple doses of imaging agent, as when reconstituted with a pertechnetate solution containing from about 1 to about 800 millicuries (mCi) of technetium-Tc99mm. (The number of doses ultimately obtained from such a kit depends upon such factors as the weight of the dosed subject and the type of tissue to be imaged.) Generally, then, a preferred kit at least comprises:

(a) an amount of the diphosphonate carrier sufficient to target the technetium in a pertechnetate solution containing from about 1 to about 800 mCi of technetium-Tc99m; and
(b) an effective amount and form of tin-containing metal with
(c) an amount of stabilizer so as to reduce the technetium in a pertechnetate solution containing from about 1 to about 800 mCi technetium-99m and to maintain the technetium in a reduced state.

See, e.g., the following U.S. patent applications filed June 10, 1982, incorporated by reference herein: U.S. patent application Ser. No. 387,135, now abandoned, "Radiographic Imaging Agents," Benedict and Van Duzee; and U.S. patent application Ser. No. 387,137, now abandoned, "Radiographic Imaging Agents," Van Duzee.

The kit compositional aspects of the present invention can be prepared by simply dry mixing the stabilizer and the optional carrier and stannous compounds with optional non-interfering agents such as sodium chloride. Such compositions are preferably placed in sterile vials fitted with a rubber septum, thereby facilitating mixing with a pertechnetate-Tc99m solution and convenient use in the hospital. The vials are preferably nitrogen-filled as an added protection against oxidation.

In another mode, kits can be provided as aqueous solutions in sterile, pyrogen-free water. Preferably, the water is deoxygenated and the composition is stored under nitrogen.

In a preferred mode, the kit compositions can be provided in freeze-dried (lyophilized) form. Such compositions are prepared by co-dissolving the optional carrier and stannous compounds and the stabilizer in an aqueous solution, and freeze-drying the composition using commercially-available lyophilization equipment. Preferably, sterile, deoxygenated water is used in processing and the product is stored under nitrogen. Although somewhat more complicated to manufacture than the dry-mixed product, the freeze-dried product offers the advantage that water-insoluble particulate matter which might be present in the raw materials can be removed by filtration prior to the freeze-drying step.

A preferred method of producing a lyophilized skeletal imaging kit includes the steps of:

(1) preparing an aqueous solution of diphosphonate carrier, stabilizer, and optional components;
(2) adjusting the solution formed in step 1 to a pH in a specific range dependent upon the particular stabilizer used; and
(3) lyphilizing the pH-adjusted solution, wherein a metal is introduced into the composition before, after, or concurrently with any step of the process. The pH may be adjusted with any pharmaceutically-acceptable acid or base. A preferred kit is produced by incorporating an ascorbate or reductate stabilizer and adjusting the carrier/stabilizer solution to about pH 6.0. If gentisate compounds are used as the stabilizer, the carrier/stabilizer solution is preferably adjusted to about pH 4.5. These processes are described in the following U.S. patent applications, filed June 10, 1982 (incorporated by reference herein): Ser. No. 387,136 now U.S. Pat. No. 4,504,462, "Process for Making Lyophilized Product Use in Skeletal Imaging," Van Duzee and Degenhardt (pH-adjusted process with ascorbate/reductate compounds; and Ser. No. 387,139, now U.S. Pat. No. 4,504,463, "Process for Making a Lyophilized Product for Use in Skeletal Imaging," Van Duzee (pH-adjusted process with gentisate compounds).

Another novel embodiment of this invention is a "contact process" wherein dry-powder kits are produced that comprise a stabilizer but contain no metal in metallic form. This process is described in concurrently filed U.S. patent application Ser. No. 447,863, now U.S. Pat. No. 4,510,125, "Process for Making a Lyophilized Radiographic Imaging Kit," Grogg, Bugaj and Bates (incorporated herein by reference). Specifically, the instant process comprises the steps of:

(1) preparing an aqueous solution of a stabilizer and, optionally, a carrier;
(2) contacting the solution formed in step 1 with a tin metal; and
(3) lyophilizing the solution.

The dry-powder imaging kit thus formed yields a stable imaging agent upon reconstitution with a pertechnetate-Tc99m solution. Preferably, the aqueous solution formed in step 1 comprises both a stabilizer and a carrier. Other optional ingredients, such as a stannous compound, can also be dissolved in the solution formed in step 1. However, the carrier, stannous and other optional compounds can be dissolved at any time prior to lyophilization.

As used herein, the term "contacting" refers to any act, process or method by which the surface of the metal is made to touch or join the aqueous stabilizer solution, including total or partial immersion of the metal in solution, rinsing the metal with solution, and touching of the metal to the surface of the solution. The exact length of time that the metal is in contact with the aqueous stabilizer solution is not critical. However, the duration of contact does affect the long-term stability of technetium-containing imaging agent formed from the dry-powder kit. Further, the method of contacting and the amount of metal used, through affecting the surface area of metal available for contact, has an effect on the stability of the technetium-based imaging agents ultimately formed. Preferred embodiments of the contact process employ complete immersion of the tin metal in the aqueous stabilizer solution for at least about thirty minutes where the total surface area of the metal is about 100 mm$^2$. (However, a contact of shorter duration can be facilitated through increasing the available surface area of metal.)

There are many methods by which the contacting step of this process may be executed. In one mode, the aqueous solution of stabilizer is made to flow over a metal-containing substrate. This flow can be accomplished through such a means as pumping the solution or by aid of gravitational force. In a second mode, the solution is placed in a vessel into which the metal is added. The solution may or may not be stirred. If stirred, laminar, non-turbulent stirring is preferred.

In a preferred mode, stannous oxide is coated onto the tin metal. The stannous oxide may be present as a naturally occurring coating on the tin metal surface, or can be incorporated by deliberate oxidation of the metal surface. Use of stannous oxide as a coating on the metal facilitates a shorter contact time necessary to produce an imaging agent with acceptable stability after reconstitution. Depending upon the amount of oxide coating present and the length of contact time, it may become necessary to renew the stannous oxide coating on a tin metal or to use a different tin metal, due to depletion or dissolution of the stannous oxide.

The pH of the aqueous stabilizer solution should, preferably, be maintained between about pH 1.0 and about pH 6.0 while in contact with the metal. More preferably, the pH of the stabilizer solution is from about pH 3.0 to about pH 3.5. After the contacting step is completed, the aqueous stabilizer solution, containing the stabilizer, optional carrier, and optional stannous compound, is lyophilized. Preferably, the pH of the stabilizer solution, after contacting with the metal but before lyophilizing, is pH optimized depending upon the particular stabilizer compound used. As in the preferred processes for making lyophilized metal-containing kits, described above, if the stabilizer is a gentisate compound, the pH of the solution is adjusted to a pH from about 4.2 to about 4.8, preferably about 4.5. If the stabilizer is an ascorbate or reductate compound, the pH should be adjusted in the range from about 5.5 to about 6.5, preferably about 6.0. The pH may be adjusted with any pharmaceutically-acceptable acid or base.

Thus, a preferred process for making a dry-powder skeletal imaging kit comprises the steps of:

(1) preparing an aqueous solution of a gentisate stabilizer, a diphosphonate carrier, and, optionally, a stannous compound;
(2) adjusting the pH of the solution formed in step 1 to a pH in the range from about 1.0 to about 6.0;
(3) contacting the solution adjusted in step 2 with a stannous oxide-coated tin metal for at least thirty minutes;
(4) separating the solution of step 3 from the metal;
(5) adjusting the pH of the solution separated in step 4 to a pH in the range from about 4.2 to about 4.8; and
(6) lyophilizing the pH-adjusted solution.

If an ascorbate or reductate stabilizer is used in the above-described process, the pH of the separated solution of step 4 should be adjusted to a pH in the range from about 5.5 to about 6.5.

An alternate embodiment of this invention consists of the use of the contact process described above to prepare a dry-powder kit that also contains tin metal. Thus, in the contact processes described above, the aqueous stabilizer solution, after contacting the metal, is not separated from the metal but the solution is lyophilized in the presence of tin metal and both the tin metal and the lyophilized stabilizer solution are placed in a vial. In one alternate mode, the stabilizer solution may be separated from the tin metal, lyophilized, and placed in a vial that already contains tin metal or that is composed entirely, or in part, of tin metal. Alternatively, the stabilizer solution can be placed in the vial, lyophilized and, subsequently, the metal can be added. Any of these procedures produce a dry-powder imaging kit that yields a stable imaging agent upon reconstitution with a pertechnetate-Tc99m solution. Imaging agents made from such tin-containing kits have longer stability, after addition of a pertechnetate-Tc99m solution, than agents made from kits that do not contain tin metal.

The kit compositions of this invention are dissolved with a pertechnetate-Tc99m isotonic solution from a commercial technetium source to yield an imaging agent suitable for intravenous injection. The stability of such imaging agents is ample under ordinary hospital conditions. Administration is preferably done within about eight hours after addition of the pertechnetate-Tc99m solution. Preferably, the concentration of reagents and technetium radionuclide is sufficient that about 1 milliliter of the solution is used in an adult of about 50-100 kg body weight. One milliliter of solution is preferably injected intravenously over a period of about 30 seconds. The total dosage of radionuclide for a sharp skeletal or myocardial infarct scan ranges from about 5 mCi to about 30 mCi, preferably from about 10 mCi to about 20 mCi. See also (incorporated by reference herein), U.S. Pat. Nos. 4,234,562, Tofe et al., issued Nov. 18, 1980; and 4,247,534, Bevan, issued Jan. 27, 1981.

The following non-limiting examples illustrate the compositions, processes, and uses of the present invention.

EXAMPLE I

A skeletal imaging agent, encompassed by the present invention, was produced with the following ingredients:

| Component | Quantity |
| --- | --- |
| tin metal foil | 5 mm × 10 mm × 0.13 mm |
| disodium salt of methane diphosphonic acid (MDP) | 5.0 mg |
| ascorbic acid | 0.84 mg |

The tin foil was placed in a vial. A solution containing the MDP carrier (adjusted to pH 6) and a solution containing the ascorbic acid stabilizer were added to the vial. One milliliter of a solution containing about 75 mCi of pertechnetate-Tc99m, eluted from a commercial technetium generator, was then added to the vial to form a skeletal imaging agent solution.

After agitation, approximately one-fourth of the solution in the vial is injected into an adult human subject weighing about 75 kg. (Care is taken so as not to draw any tin metal into the injection syringe) Excellent skeletal images are then obtained using a scintillation camera.

In the kit prepared above, erythorbic acid, sodium ascorbate, reductic acid, sodium reductate, 6-bromo-6-deoxy ascorbate, 5-methyl reductic acid, sodium 5-methyl reductate, and nicotinic acid and nicotinamide complexes thereof are substituted, respectively, for ascorbic acid, with substantially similar results.

EXAMPLE II

A collecting vial containing 0.1 mg of sodium gentisate is placed at the eluate orifice of a pertechnetate-Tc99m generator. Saline eluate is collected in the vial and completely dissolves the sodium gentisate.

Approximately 5 ml (200 mCi) of the pertechnetate-Tc99m solution, with the dissolved sodium gentisate, is added to a vial containing 4.0 g of 30 mesh granular tin metal and 200 mg sodium glucoheptonate. After thorough mixing, a stable skeletal imaging agent suitable for intravenous injection into a human patient is prepared.

Approximately 0.5 ml of the agent is injected into an adult human subject. After about one hour, scintigraphy of the subject yields brain and renal images.

EXAMPLE III

An imaging composition is formulated with the following components:

| Component | Quantity |
| --- | --- |
| sodium pyrophosphate | 10.0 mg |
| sodium trimetaphosphate | 30.0 mg |
| gentisyl alcohol | 0.20 mg |
| tin metal foil | 5 mm × 5 mm × 0.13 mm |

(The sodium pyrophosphate is as described above, and in U.S. Pat. No. 4,016,249, Adler, et al., issued Apr. 5, 1977.)

The composition is formed by simple admixture of the listed ingredients. A stable imaging agent is formed upon addition of about 5 ml of a pertechnetate-Tc99m solution, as described in Example I.

In the above example, hydroquinone can be substituted for gentisyl alcohol, with substantially similar results.

EXAMPLE IV

An imaging kit was prepared with the following components:

| Component | Bulk Solution | Vial |
| --- | --- | --- |
| sodium thiosulfate | 200 mg | 2.0 mg |
| disodium edetate (EDTA) | 200 mg | 2.0 mg |
| gelatin | 1810 mg | 18.1 mg |
| gentisic acid | 84 mg | 0.84 mg |
| tin metal foil | — | 9.5 mm × 6.4 mm × 0.13 mm |

A bulk solution was prepared by admixing the thiosulfate, EDTA, gelatin, and gentisic acid in 100 ml of sterile water. The solution was gently heated to achieve total dissolution of all components. A one milliliter aliquot of the bulk solution (at pH 4.4) was transferred to a sterile, pre-frozen vial. The tin metal foil was then added to the vial. The vial was lyophilized for about 18 hours and stoppered under vacuum.

An imaging agent is prepared from this kit by adding saline eluate from a pertechnetate-Tc99m generator. The sulfur colloid imaging agent thereby formed is injected into a biologic subject and images are obtained of the liver, spleen and bone marrow.

EXAMPLE V

A composition encompassed by this invention was made with the following components:

| Component | Quantity |
| --- | --- |
| whole red blood cells (packed) | 2.5 ml |
| gentisic acid | 0.84 mg |
| tin metal foil | 9.5 mm × 6.4 mm × 0.13 mm |
| pertechnetate-Tc99m | 2.25 mCi |

The tin metal and a 1.0 ml saline solution of the gentisic acid were added to a 5.0 ml saline suspension of the blood cells, The resulting mixture was agitated to ensure complete mixing. The pertechnetate was then added and the mixture agitated for about one minute. The blood cells were then washed three times with saline, 5.0 ml per wash, to remove the technetium that was not bound within the cells. The resulting agent is then injected into a biologic subject and blood pool images are obtained.

EXAMPLE VI

A blood pool imaging agent was prepared comprising the following components:

| Component | Quantity |
| --- | --- |
| bovine serum albumin (BSA) | 5.0 mg |
| gentisic acid | 4.2 mg |
| tin metal foil | 9.5 mm × 6.4 mm × 0.13 mm |

The BSA and gentisic acid were added, in powder form, to a vial containing the tin metal. The powders were dissolved by adding 4.5 ml of a sodium phosphate saline solution buffered to pH 4.5 with hydrochloric acid. After complete dissolution of the BSA and gentisic acid, 0.5 ml of a pertechnetate-Tc99m solution (approximately 2.5 mCi) was added to form an Imaging agent, The agent, comprising about 1.0 mg protein and 0.84 mg gentisic acid per milliliter, yields blood pool images when injected into a biologic subject and the subject is scintigraphed.

EXAMPLE VII

An imaging agent for detecting and localizing tumors containing carcinoembryonic antigen (CEA) is prepared and used in a manner similar to that described in Goldenberg, et al., "Radioimmunodetection of Cancer with Radioactive Antibodies to Carcinoembryonic Antigen," *Cancer Research*, 40, 2984–2992 (1980) (incorporated by reference herein) except that the CEA-antibody is labelled with technetium-99m. In particular, purified goat immunoglobulin G is labelled with about 2.5 ml of technetium-99m, using tin metal as a reductant for the technetium, in the procedure described in Example VI, above, wherein the immunoglobulin G is substituted for bovine serum albumin. The imaging agent thus obtained is injected into an adult human subject having colorectal cancer and the location of the tumor determined by standard scintigraphic methods. This imaging agent also localizes ovarian cancers, cervical cancers and lung cancers.

EXAMPLE VIII

The compositions and processes of this invention are used in a competitive binding radioimmunoassay of serum insulin through a procedure similar to that described in Yalow, et al., "Immunoassay of Plasma insulin," *Methods of Biochemical Analysis*, 12, 69–96 (1964) (incorporated by reference herein). In particular, a known quantity of insulin is labelled with technetium-99m by the method described in Example VI, above, substituting the insulin for bovine serum albumin, yielding technetium-labelled insulin ("insulin/Tc").

Into 13 vials is aliquoted 50 microliters of a Veronal buffer solution containing 0.5 nanograms per milliliter of insulin/Tc, into each of the first 12 vials is aliquoted 50 microliters of a Veronal buffer solution, each aliquot having a known concentration of unlabelled insulin varying from 0.025 ng/ml to 2.0 ng/ml. Into the remaining vial of insulin/Tc is introduced an aliquot of serum with an unknown concentration of insulin.

A 1:6000 dilution of guinea pig anti-porcine insulin antiserum is prepared and 50 microliter aliquots thereof are added to each of the 13 vials prepared above. The vials are then allowed to incubate for 6 hours, at room temperature, during which time the antiserum binds the insulin.

After incubation, a solution containing a second antibody, goat anti-guinea pig gamma globulin, is added to each vial. The vials are incubated for 1 hour at room temperature to allow binding of the goat antibody to the guinea pig antibody. The vials are then centrifuged and the supernatent removed from the pallet that contains the bound guinea pig anti-porcine insulin antibody, The radioactivity of the insulin contianing pellets are measured through the use of a gamma counter. Analysis of the data, compensating for the radioactive decay of the technetium-99m during the course of the experiment, is made yielding the relative radioactivity of the pellet from each of vials 1 through 12 as a function of the known insulin concentration in each vial, (Since the insulin/Tc and unlabelled insulin compete for a small quantity of insulin-specific antibody, the amount of insulin/Tc present at equilibrium and, hence, the radioactivity of the pellet, varies inversely with the amount of unlabelled insulin present.) The concentration (and amount) of insulin present in the unknown sample placed in vial 13 is determined by comparison and extrapolation of the data generated from the known samples in vials 1 through 12.

EXAMPLE IX

A skeletal imaging kit is formulated with the following components:

| Component | Bulk Solution | Vial |
| --- | --- | --- |
| disodium HMDP | 300 mg | 3.0 mg |
| gentisic acid | 84 mg | 0.84 mg |
| sodium chloride | 3.0 g | 30.0 mg |
| stannous chloride | 3.2 mg | 0.032 mg |
| 3.2 mm tin shot | — | 5.5 g |

A bulk solution is prepared by admixing the HMDP carrier, gentisic acid stabilizer, stannous chloride, and sodium chloride in sterile nitrogen-purged (deoxygenated) water. A sodium hydroxide solution is added so as to adjust the bulk solution to pH 4.5. Sterile, nitrogen-purged water is added to bring the volume to 100 ml.

Tin shot (20 pieces, 5.5 g, with a surface area of approximately 600 mm²) is added to each vial. The tin is sterilized by heating the vials with tin to 250° C. for approximately 4 hours. (The tin, after heating, is completely coated with stannous oxide.) The vials are then cooled.

One milliliter aliquots of the bulk solution are transferred to sterile vials which are kept under a nitrogen blanket in order to exclude oxygen. The vials are frozen under dry ice and dried under vacuum for 3 hours in a commercial lyophilization apparatus. The vials are gradually heated to 25° C. and lyophilized for an additional 16 hours. The vials, containing lyophilized product, are stoppered and sealed under vacuum.

An imaging agent is prepared using this kit by adding about 5 ml of a pertechnetate-Tc99m physiological saline with an activity of about 75 mCl, from a commercial technetium source. The vial is agitated until the components are dissolved. About 1 ml of the agent is slowly injected, over a period of about 30 seconds, into an adult human subject weighing about 75 kg. Excellent skeletal images are then obtained using a scintillation camera.

In the kit prepared above, methane-N-methylaminodiphosphonic acid, methane-N,N-dimethylaminodiphosphonic acid, ethane-1-hydroxy-2-amino-1,1-diphosphonic acid, and the monosodium salts thereof, and ethane-1-hydroxy-1,1-diphosphonic acid and the disodium salt thereof are, respectively, used instead of disodium HMDP, with substantially similar results.

EXAMPLE X

A kit was made, using the contact process of this invention, comprising the following components:

| Component | Bulk Solution | Vial |
|---|---|---|
| disodium HMDP | 33.0 mg | 3.0 mg |
| gentisic acid | 9.2 mg | 0.84 mg |

A bulk solution was prepared by dissolving the HMDP and gentisic acid in about 11.0 ml sterile, nitrogen-purged water. A "column" was prepared using a 10 cc Becton-Dickson syringe packed with 3.6 g of 30 mesh granular tin on a glass wool substrate. The bulk solution (at pH 3.2) was poured on top of the granular tin and allowed to stand in contact with the metal for thirty minutes. The bulk solution was then withdrawn from the syringe/column and filtered.

The pH of the bulk solution was adjusted to a pH of 4.5 with a sodium hydroxide solution. A one milliliter aliquot of the pH-adjusted solution was placed into a sterile vial and lyophilized for about 17 hours, yielding a dry-powder imaging kit.

Excellent skeletal images are obtained when this kit is used to prepare an imaging agent and the agent is injected, as in Example IX.

In the above example, hydroquinone, gentisyl alcohol, the sodium gentisate are substituted, respectively, for gentisic acid, with substantially similar results.

EXAMPLE XI

A kit was made, using the contact process of this invention, comprising the following components:

| Component | Bulk Solution | Vial |
|---|---|---|
| disodium HMPD | 300 mg | 3.0 mg |
| gentisic acid | 84 mg | 0.84 mg |

A bulk solution was prepared by dissolving the HMDP and gentisic acid in 100 ml water. The bulk solution (at pH 3.2) was placed in a 250 ml capped Erlenmeyer flask containing 36 g of 30 mesh granular tin. The bulk solution and tin were slurried by turbulent, non-laminar stirring, under atmospheric conditions, for 1.5 hours.

The bulk solution was removed from the granular tin, filtered, and pH adjusted to pH 4.5. A one milliliter aliquot of bulk solution was placed in a sterile vial and lyophilized. The resulting dry-powder imaging kit yields excellent skeletal images when reconstituted with a pertechnetate-Tc99m solution and injected as described in Example IX.

EXAMPLE XII

Imaging kits are prepared using the contact process of this invention, comprising the following ingredients:

| Component | Bulk Solution | Vial |
|---|---|---|
| disodium HMDP | 1.5 g | 3.0 mg |
| ascorbic acid | 500 mg | 1.0 mg |
| sodium chloride | 15 g | 30 mg |

A bulk solution is prepared by dissolving the HMDP, ascorbic acid, and sodium chloride in 500 ml deoxygenated water. The pH of the bulk solution is adjusted to pH 3.5 using hydrochloric acid. The solution is then pumped, at a flow rate of 100 ml min$^{-1}$, through a cylindrical glass column (30 cm long and 5.8 cm diameter) packed with 1800 g of 30 mesh granular tin that is washed with acetone and has a coating of stannous oxide. After 3.5 hours, the solution is filtered and adjusted to pH 6.0 using sodium hydroxide.

One milliliter aliquots of the pH-adjusted solution are then placed in sterile vials and lyophilized using standard lyophilization procedures. Excellent skeletal images are obtained when the resulting kits are used to prepare imaging agents and the agents are injected as described in Example IX.

In the above example, erythorbic acid, sodium ascorbate, sodium erythorbate, reductic acid, sodium reductate, 5-methyl reductic acid, sodium 5-methyl reductate, 6-bromo-6-deoxyascorbic acid, sodium 6-bromo-6-deoxyascorbate, and the nicotinic acid and nicotinamide complexes thereof are used, respectively, instead of ascorbic acid, with substantially similar results.

EXAMPLE XIII

Dry-powder imaging kits are made according to this invention having the composition and quantities detailed in Example VII. Kits are made by the process of Example VII but, after the lyophilization of the product, a sterilized piece of tin foil, measuring about 5 mm×5 mm, is added to each vial. The vials are then sealed and stoppered.

Imaging agents made from these kits have excellent skeletal imaging properties when reconstituted and injected into a biologic subject as described in Example IX. In the above example, the inside of the vials are coated with tin metal (through standard deposition procedures, described above) before the solution is added and lyophilized, rather than adding a piece of tin foil after lyophilization, with substantially similar results.

EXPERIMENT I

Six kit vials were prepared according to the process described in Example I, above*. The composition of the vials were as follows.

| Vial | Component | Quantity |
|---|---|---|
| 1 & 2 | disodium MDP | 5.0 mg |
|  | tin foil | 5 mm × 10 mm × 0.13 mm |
| 3 & 4 | disodium MDP | 5.0 mg |
|  | 30 mesh granular tin | 150 mg |
| 5 & 6 | disodium MDP | 5.0 mg |
|  | ascorbic acid | 0.84 mg |
|  | tin foil | 5 mm × 10 mm × 0.13 mm |

The tin in all vials, except for vial 3, was pretreated by immersion in concentrated hydrochloric acid followed by thorough rinsing with ethanol.

Imaging agents were formed by addition of about 75 mCi pertechnetate-Tc99m, in solution, to each of kits 1, 3 and 5, and about 365 mCi pertechnetate-Tc99m, in solution, to each of kits 2, 4 and 6. The amount of unreduced "free" technetium present in each kit vial was determined, by thin layer chromatography, as a function of time. This data is presented in Table 1, below, wherein "Tc" is the approximate quantity (mCi) of pertechnetate-Tc99m introduced into each vial, "Time" is the time elapsed between introduction of the radioisotope into each kit vial and the measurement of free pertechnetate remaining, and the data is expressed as the percent of original pertechnetate that was reduced, i.e., 100% - % free pertechnetate at the time of measurement.

TABLE 1

| | | % Reduced at Time (in minutes) | | | | | | | |
|---|---|---|---|---|---|---|---|---|---|
| Vial | Tc | 0 | 10 | 20 | 30 | 60 | 120 | 180 | 240 | 300 |
| 1 | 75 | 97 | 96 | 93 | 94 | 92 | 94 | 94 | 96 | 97 |
| 2 | 365 | 49 | 51 | 54 | 60 | 59 | 60 | 61 | 63 | 64 |
| 3 | 75 | 14 | 30 | 63 | 85 | 98 | 98 | 98 | 97 | 95 |
| 4 | 365 | 99 | 95 | 92 | 90 | 85 | 79 | 76 | 75 | 74 |
| 5 | 75 | 99 | 100 | 100 | 100 | 100 | 100 | 100 | 100 | 100 |
| 6 | 365 | 99 | 100 | 100 | 100 | 100 | 100 | 100 | 100 | 100 |

This data demonstrates the significantly better performance of the combination of tin metal and a stabilizer as compared to tin metal alone as a reducing system for pertechnetate. The complete reduction of technetium facilitated by the compositions of the present invention (exemplified by vials 5 and 6) not only generates more technetium-labelled carrier in imaging agents, but correspondingly eliminates the presence of the free pertechnetate in such agents that has a deliteriuos effect on the biological performance of imaging agents. Thus, imaging agents incorporating the combination of tin metal and a stabilizer have superior imaging qualities.

EXPERIMENT II

Vials were prepared * according to a process similar to that described in Example I, above. The final composition of the vials was as follows:

| Vial | Component | Quantity |
|---|---|---|
| 1 | disodium HMDP | 3.0 mg |
|  | gentisic acid | 0.84 mg |
|  | tin metal foil | 9.5 mm × 6.4 mm × 0.13 mm |
| 2 | disodium HMDP | 3.0 mg |
|  | ascorbic acid | 0.97 mg |
|  | tin metal foil | 9.5 mm × 6.4 mm × 0.13 mm |
| 3 | disodium HMDP | 3.0 mg |
|  | sodium nitrate | 0.50 mg |
|  | tin metal foil | 9.5 mm × 6.4 mm × 0.13 mm |
| 4 | disodium HMDP | 3.0 mg |
|  | sodium nitrate | 4.0 mg |
|  | tin metal foil | 9.5 mm × 6.4 mm × 0.13 mm |

Kit vial 4 was prepared and tested in a separate experiment run than vails 1 through 3.

Kits were prepared by adding solutions of HMDP, and ascorbic acid, gentisic acid, sodium nitrate or sodium nitrite, to a vial. The pH of each vials 3 and 4 was adjusted to 1.5 as suggested in European Patent Application No. 46,067, Brockas, et al., published Feb. 17, 1982 (incorporated by reference herein). The pH of vial 1 was adjusted to 4.5 and the pH of vial 2 was adjusted to 6.0. The tin metal foil was then added to each vial.

Imaging agents were then formed by addition of about 395 mCi of pertechnetate-Tc99m solution to each of kits 1 through 3. Approximately 88 mCi of pertechnetate-Tc99m was added to vial 4. Table II, below, present the amount of pertechnetate bound as a function of time, as in Table I, above.

| | | % Reduced at Time (in minutes) | | | | | | | |
|---|---|---|---|---|---|---|---|---|---|
| Vial | TC | 0 | 10 | 20 | 30 | 45 | 60 | 120 | 240 | 300 |
| 1 | 395 | 38 | 65 | 90 | 97 | 99 | 100 | 100 | 100 | 100 |
| 2 | 395 | 74 | 99 | 100 | 100 | 100 | 100 | 100 | 100 | 100 |
| 3 | 395 | 22 | 29 | 42 | 53 | 60 | 71 | 89 | 96 | 99 |
| 4 | 88 | 2 | — | — | 15 | — | 32 | — | 94 | — |

This data demonstrates the significantly better performance of the combination of tin metal and the stabilizer of this invention as compared to tin metal and nitrate or nitrite compounds. The compositions of this invention (exemplified by vials 1 and 2) yield more rapid and more complete reduction of technetium resulting in improved biological performance of such agents encompassed by this invention.

What is claimed is:

1. A composition, useful in the preparation of technetium-99m-based imaging agents, comprising:
   (a) a metal selected from the groups consisting of tin and tin-containing alloys, said metal being employed in an amount effective to reduce the technetium to be added to form an imaging agent; and
   (b) a stabilizing amount of stabilizer selected from the group consisting of gentisate, ascorbate, and reductate compounds, and mixtures thereof.

2. A composition, as in claim 1, further comprising a tissue-specific carrier.

3. A composition, as in claim 1, further comprising a stannous compound.

4. A composition, as in claim 1, wherein said stabilizer is selected from the group consisting of gentisic acid and pharmaceutically-acceptable salts thereof.

5. A composition, as in claim 1, wherein said stabilizer is selected from the group consisting of ascorbic acid, erythorbic acid, and the pharmaceutically-acceptable salts and esters thereof.

6. A composition, as in claim 2, wherein said tissue-specific carrier is an organophosphonate.

7. A composition, as in claim 6, wherein said organophosphonate is selected from the group consisting of methane diphosphonic acid, hydroxymethane diphosphonic acid, ethane-1-hydroxy-1,1-diphosphonic acid, methane amino diphosphonic acid, methane-N-methyl amino diphosphonic acid, methane-N,N-dimethylamino diphosphonic acid, propane-1-hydroxy-3-amino-1,1-diphosphonic acid, ethane-1-hydroxy-2-amino-1,1-diphosphonic acid, and the pharmaceutically-acceptable salts and mixtures thereof.

8. A composition, as in claim 2, wherein said tissue-specific carrier is a protein, peptide, or amino acid.

9. A composition, as in claim 3, wherein said stannous compound is selected from the group consisting of stannous chloride, stannous fluoride, stannous citrate, stannous tartrate, stannous oxide, and mixtures thereof.

10. A composition, as in claim 3, wherein said stannous compound is an organophosphonate.

11. A composition, as in claim 9, wherein said metal is coated with stannous oxide.

12. A composition, as in claim 9, wherein said stannous compound is stannous chloride.

13. A composition, as in claim 9, comprising:
(a) a metal selected from the group consisting of tin and tin-containing alloys;
(b) a stabilizer selected from the group consisting of gentisate, ascorbate, and reductate compounds, and mixtures thereof;
(c) a diphosphonate tissue-specific carrier; and
(d) a stannous compound; wherein the molar ratio of a diphosphonate carrier to said stannous compound is at least 65:1.

14. A composition, useful in the preparation of technetium-99m-based imaging agents, comprising:
(a) a stabilizer selected from the group consisting of gentisate, ascorbate and reductate compounds, and mixtures thereof; dissolved in
(b) an oxidized pertechnetate solution; and
(c) a metal selected from the group consisting of tin and tin-containing alloys.

* * * * *